(12) United States Patent
Lindequist (10) Patent No.: US 6,567,681 B1
(45) Date of Patent: May 20, 2003

(54) METHOD AND ARRANGEMENT FOR DETERMINING WHERE TO POSITION FIXATION MEANS

(75) Inventor: Stig Lindequist, Saltsjöbaden (SE)

(73) Assignee: Medical Robotics i Stockholm AB, Stockholm (SE)

(*) Notice: Subject to any disclaimer, the term of this patent is extended or adjusted under 35 U.S.C. 154(b) by 0 days.

(21) Appl. No.: 09/647,451

(22) PCT Filed: Mar. 30, 1999

(86) PCT No.: PCT/SE99/00522

§ 371 (c)(1),
(2), (4) Date: Nov. 13, 2000

(87) PCT Pub. No.: WO99/49786

PCT Pub. Date: Oct. 7, 1999

(30) Foreign Application Priority Data

Apr. 1, 1998 (SE) .............................................. 9801168

(51) Int. Cl.⁷ ................................................ A61B 5/05
(52) U.S. Cl. ...................... 600/407; 606/130; 378/20; 378/205
(58) Field of Search .............................. 600/407, 427; 606/96, 97, 130; 378/20, 205

(56) References Cited

U.S. PATENT DOCUMENTS 5,772,594 A * 6/1998 Barrick ........................ 600/407
6,285,902 B1 * 9/2001 Kienzle, III ................. 600/427

OTHER PUBLICATIONS

Troccaz, Jocelyne et al. "First International Joint Conference Computer Vision, Virtual Reality and Robotics in Medicine and Medical Robotics and Computer–Assisted Surgery," CVRMed–MRCAS'97', Mar. 1997, pp. 565–572.

* cited by examiner

Primary Examiner—Peter Nerbun
(74) Attorney, Agent, or Firm—Pillsbury Winthrop LLP

(57) ABSTRACT

The present invention is comprised of a method for determining, in three dimensions, where to position fixating means (32) in a hip bone fracture structure (30) by pre-surgery analysis of at least one anteroposterior and one lateral digitized radiograph of a fracture. The method is applied to control an arrangement (40) with a tool for drilling in the correct direction in order to accomplish a best possible healing of a fractured hip bone structure (30).

21 Claims, 5 Drawing Sheets

METHOD AND ARRANGEMENT FOR DETERMINING WHERE TO POSITION FIXATION MEANS

TECHNICAL FIELD

The present invention relates to a method and an arrangement determining where to position fixating means for hip fractures and an arrangement for providing attachment of said fixating means controlled by data from said method.

BACKGROUND ART

Present methods regarding, for example, hip fracture surgery involves a great deal of craftsmanship. A patient with an injured leg is placed supine on a fracture table and a reduction maneuver is carried out. The foot of an injured leg is firmly fixed in a specially built shoe. Traction and rotation are applied until the fracture is reduced.

A fixation of an injured leg is normally so firm that no movement will take place unless a substantial force is applied to the leg. A mobile X-ray apparatus, a "C-arm", with two perpendicular radiographs, the anteroposterior (AP) and the lateral (Lat) projections, checks quality of reduction. The result of a reduction can only be judged through said at least two radiographs, and no correction for variations in hip rotation is possible.

Screws are inserted in order to fixate the fractured bone parts. The screws are introduced by a hand-held drill which opens up guide holes for the screws, whereby a surgeon has to judge the position of the drill from said two perpendicular radiographs and manually adjust the position of the drill in three dimensions, which is a very difficult task.

Unfortunately, the insertion of screws very often has to be repeated. Repeated trials of insertion destroy the bone structure in the femoral neck.

To be able to check the quality after a performed hip fracture surgery a method was developed for determining the post surgery position of a fixating means. It was introduced by the inventor of the present invention in his thesis "Internal Fixation of Femoral Neck Fractures", Stockholm 1993, ISBN 91-628-0804-4. Nevertheless, the method has only been used for post-surgery quality checks and scientific statistics, and it has not occurred to or been obvious to any person skilled in the art to modify the method so it can be used in determining how and where to drill in a femoral bone fracture in order to attach fixating means and facilitate healing of said fracture in a best possible way.

Today, orthopedic surgery has promulgated towards sophisticated hi-tech implants being manually inserted through in-precise techniques. To manually insert implants is a task for a highly skilled orthopedic surgeon with, for example, 10 years of training in the present medical field.

For diagnosis groups, where a great number of injuries is accumulated, the result of performed surgery is less satisfactory than it could be. Hip fractures belong to such a group, whereby about 18,000 incidents/year occur in Sweden alone, 9,000 cervical and 9,000 pertrochanteric, to a cost of approximately SEK 1.4 billions.

Despite of the more than 100 different fixating methods developed for this kind of fractures, the result of performed surgery is relatively poor. As much as approximately 35% of all cervical fractures do not heal, and 20% of them have to be re-operated within a time period of 1–2 years. For pertrochanteric fractures the same rates are 10% and 4% respectively. Every re-surgery approximately costs SEK 185,000.

It is agreed with among surgeons and other experts that the main reason for the high percentage of re-surgery is an inadequately positioning of the fixating screws, which hold the fracture together during the following healing process, see "Fixation of femoral neck fractures: comparison of the Uppsala and Von Bahr screws." By Rehnberg & Olerud, Acta Orthop Scand 60, 1989, p. 579–584.

Considering the costs of SEK 185,000 for one re-surgery, a decrease in the rate of such surgery with 50% would gain a save of SEK 160 millions a year in surgery costs. A bigger Swedish Hospital would save approximately SEK 8 millions, not to say what is gained in relief for fractured patients.

A known arrangement to support surgery is the so-called ROBODOC® Surgical Assistant System. The ROBODOC® robot is able to precisely prepare a femoral channel for placement of a cementless prosthesis.

Due to the manual surgery technique involved in surgery relating to bone fractures and judgements made from said radiographs in real time during surgery/surgical treatment without any tools for performing analysis, the X-ray radiation will be unnecessary high for patients and personnel serving during surgery.

It would be an advantage therefore, to provide a method and an arrangement that can aid a surgeon in preparing and supporting orthopedic surgery. Such a method and arrangement are set forth through attached independent claims. Specific embodiments of the invention are introduced through the attached dependent claims. Hence the method and arrangement of the present invention and details thereof provides such advantages.

SUMMARY OF THE DISCLOSED INVENTION

The present invention generally relates to a method used for determining where to position fixating means or fixation devices in a hip fracture and an arrangement used to aid surgeons. It is controlled by data from said method. Said method brings about data out of conventional radiographs taken to detect fractures. Hence, the method is applied after diagnosis and before any medical treatment has taken place.

Accordingly, the present invention provides a method for determining, in three dimensions, where to position fixating means in a hip fracture by pre-surgery analysis of at least one anteroposterior and one lateral digitized radiograph of said fracture. It comprises the following steps:

determining a construed femoral shaft axis out off said graphs from at least two midpoints on said shaft axis and drawing a line through said midpoints;

determining a construed femoral neck axis from at least two midpoints on said neck axis and drawing a line through said midpoints;

determining femoral neck angles;

determining a femoral head diameter out off said graphs by placing a circle over the perimeter of the femoral head;

determining a femoral neck diameter out off said radiographs by drawing a line, perpendicular to the femoral neck axis, at the intersection of the femoral head sphere and the central femoral neck axis;

scaling and rotating said radiographs to a predefined size and position, using an angle between the femoral shaft and an Y-axis in said digitized radiographs, and said diameter of the femoral head in both the AP and Lat projections;

determining the distance from said neck axis and the center of said femoral head perpendicular to the femoral neck-axis, representing a remaining displacement of the hip fracture which is implicitly known from said head diameter;

determining the height of a medial cortex out off the anteroposterior graph; displaying said femoral neck angles;

constructing and displaying cross-sections of the femoral head and neck with a predetermined degree of accuracy, rotating said cross-sections of the femoral head and neck in order to determine a degree of derotation of the hip, imposed by the fracture, displaying the degree of hip rotation in said anteroposterior and lateral radiographs; and using said steps in an arrangement in order to determine a position, in three dimensions for attachment of said fixating means and to pre-adjust a tool to work in said position.

In one embodiment, femoral neck angels are displayed as lines and numerical values i said digitized graphs, said lines are automatically re-drawn if the value is changed.

Another embodiment comprises that symbols for said fixating means are placed within the cross-section of the femoral neck.

A still further embodiment includes a warning function, which is activated if said fixating means are placed outside the head or neck in said digitized radiographs.

Fixating means for attachment are automatically displayed in said cross-sections with relation to made measurements according to one embodiment of the present invention.

A still further embodiment provides means for putting down symbols for fixating means in the digitized radiographs.

Yet another embodiment of the present invention comprises that said lines are regression lines drawn from at least three midpoints.

The arrangement according to the present invention provides for attachment of fixating means in a hip fracture, through analyzing at least one anteroposterior and one lateral digitized radiographs of said fracture. It comprises:

a measurement means for determining the femoral shaft axis out off said graphs from at least two midpoints on said shaft axis, and drawing a line through said midpoints;

a measurement means for determining the femoral neck axis from at least two midpoints on said neck axis and drawing a line through said midpoints;

a measurement means for determining femoral neck angels;

a measurement means for determining a femoral head diameter out off said graphs by placing a circle over the perimeter of said femoral head;

a measurement means for determining a femoral neck diameter out off said radiographs by drawing a line, perpendicular to the femoral neck axis, at the intersection of a femoral head sphere and a central femoral neck axis;

a driver means or function for scaling and rotating said radiographs to a predefined size and position, using an angle between the femoral shaft and an Y-axis in said digitized radiographs, and said diameter of the femoral head in both the AP and Lat projections;

a measurement means for determining the distance from the femoral neck axis to the center of said femoral head perpendicular to the femoral neck-axis, representing a remaining displacement of the fracture, which is implicitly known from said femoral head diameter;

a measurement means for measuring the height of the medial cortex out off said anteroposterior radiographs;

a display means for displaying said neck angles;

a display means for providing displays of cross-sections of said femoral head and femoral neck with a predetermined degree of accuracy, a driver means or function for rotating said cross-sections of the femoral head and neck in order to determine a degree of hip derotation between said head and neck, imposed by the fracture;

a display means for displaying said hip rotation in said anteroposterior and lateral radiographs; said means providing control input to a robot with tool means on said robot for working in a direction given by said control input, and distortion correcting means compensating for x-ray distortion.

In one embodiment, the femoral neck angles are displayed, by said means for displaying, as lines and numerical values in said digitized graphs, said lines are automatically redrawn by graphic means if the value is changed.

Another embodiment includes that symbols for said fixating means are placed within the cross-section of the femoral neck and displayed by said means for displaying.

A further embodiment activates a warning function if said fixating means are placed outside of the femoral head or neck in said digitized radiographs.

A still further embodiment includes that fixating means for attachment is automatically displayed in said graphs with relation to made measurements.

Means are provided for putting down symbols for fixating means in the digitized radiographs in one embodiment of the present invention.

Yet another embodiment of the present arrangement comprises that said lines are regression lines drawn from at least three midpoints.

BRIEF DESCRIPTION OF THE DRAWINGS

For a more complete understanding of the present invention and for further objectives and advantages thereof, reference may now be had to the following description in conjunction with the accompanying drawings, in which.

DETAILED DESCRIPTION OF PREFERRED EMBODIMENTS

In order to accomplish a better determination of where to place fixating means, such as screws, pins, nails etc., on fractured bone parts, the present invention introduces a method specifically developed for the task. The method and arrangement, herein disclosed for hip fractures, are shown for purposes of illustration only and are not limiting of the present invention.

With the technique used in the present invention it is possible to achieve an accuracy of ±1.0 mm when attaching fixating screws in hip fracture surgery, and in addition determining the screw length, screw fixating angle, and dislocation degree of the fracture. According to the invention, said method provides means for storing digitized radiographs graphs from performed surgery and patient records in a database for quality checks and scientific research.

In radiographs of femoral neck fractures in accordance with prior art, the position of a pin or screw in relation to a construed femoral neck axis can be determined by measuring the distances from a discretionary point to a construed femoral neck axis, located at the same distance from the femoral head center in both the AP and lateral projections, to the pin or screw. The exact position is obtained if the following criteria are fulfilled:

1. The anterioposterior and lateral radioplates are parallel to the femoral neck axis and perpendicular to each other, and the anterioposterior radioplate is parallel to the femoral shaft axis.
2. The directions of the central X-ray beams in the anterioposterior and lateral projections are perpendicular to the femoral neck axis.
3. The degrees of magnification in the anterioposterior and lateral projections are equal.

A reversed method, i.e., it is determined where to place the pin or screw in the best possible way, is introduced through the present invention.

By using an image intensifier to adjust for the position of the femoral neck in space, the criteria nos. 1–3 can be fulfilled. This is time-consuming, however, and impracticable in routine examinations. In routine radiographs of internally fixed femoral neck fractures, the rotation of the hip varies in successive examinations and also in successive exposures, i.e. criteria nos. 1–3 above is not fulfilled. In order to determine the position of where to put pins/screws out off such radiographs, the rotated projections must be derotated to straight anterioposterior (AP) and lateral (Lat) projections. This is intuitively accomplished when a routine radiograph is interpreted, but this derotation is subjective and non-reproducible.

However, by determining the derotation angle omega ($\Omega$) the rotation of the hip can be compensated for in a reproducible way.

Figure 1:
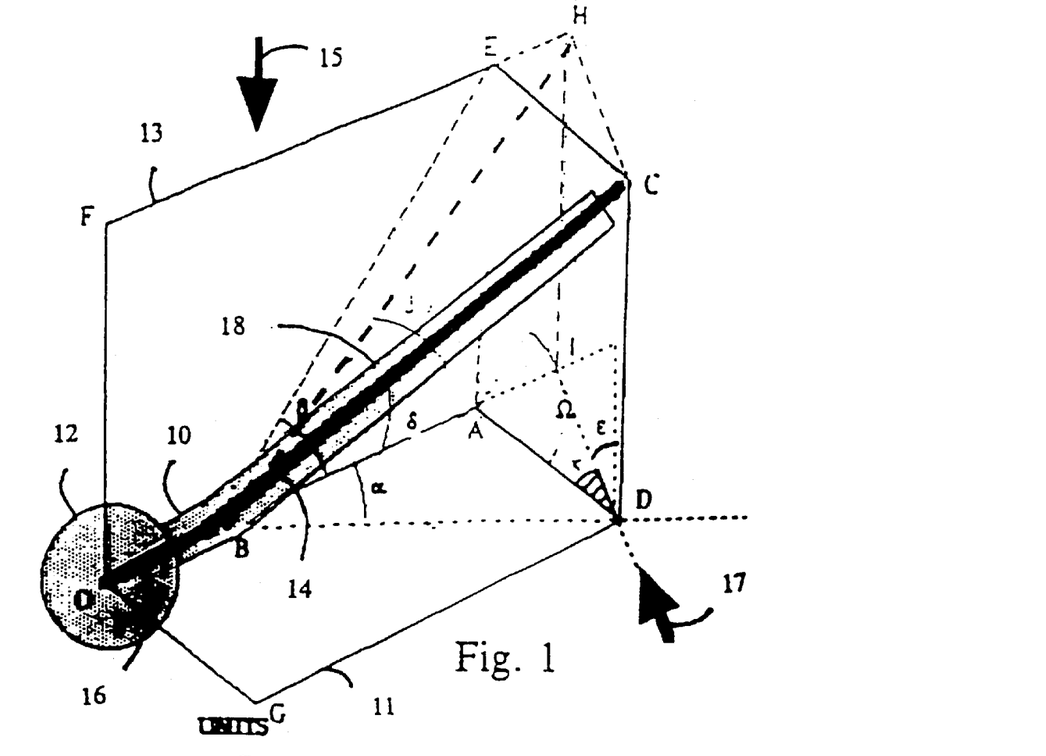
FIG. 1 schematically illustrates a femoral bone structure in perspective view, indicating symbols for mathematical calculation in accordance with prior art.

A femoral bone structure in perspective view marked up with symbols for mathematical calculation is schematically illustrated in FIG. 1. A method used for determining where fixating means have been placed after a performed surgery in hip fractures, derived from FIG. 1, is prior art, as stated above. Such a method was introduced and used by the inventor of the present invention in his study "Internal Fixation of Femoral Neck Fractures", Stockholm 1993, ISBN 91-628-0804-4. Nevertheless, the method has been used only for post-surgery quality checks and scientific statistics, see "Quality of Reduction and Cortical Screw Support in Femoral Neck Fractures", by Stig Lindequist and Hans Törnkvist, Journal of Orthopaedic Trauma, Vol. 9, No. 3, pp. 215–221, 1995 Raven Press Ltd, New York. A reversed method according to the present invention can be used in determining how and where to drill in a femoral bone fracture in order to facilitate healing of said fracture in a best possible way.

Despite the fact that the position of the fixation means in femoral neck fractures is considered to be of great importance for the outcome of a performed surgery, no other method of determining this position with a known degree of accuracy has been found in the literature.

It is a known fact that fixating means, as for example screws, are to be placed as adjacent to the femoral neck bone structure (the cortex) 10 as possible, and centered in the femoral head 12 so that a fractured neck 10 can bear relatively heavy loads. Loads of 1500 N is common. This should be considered along with elderly peoples deteriorated content of marrow inside the bone structure, which emphasis the importance of the screws being placed adjacent to the cortex.

"A Simple biplanar method of measuring femoral anteversion and neck-shaft angle" by Ogata K and Goldsand E M, J Bone Joint Surg (Am), 1979, 61:846–51, and "Radiographic measurements of the femoral anteversion, Acta Orthop Scand, 1983; 54: 141–46 by Herrlin and Ekelund, describes how the anteversion angle $\theta$ (not shown) and the neck-shaft angle $\delta$ can be calculated from the measured cerovicofemoral angles $\alpha$ and $\beta$, and the inclination angle $\epsilon$. According to their methods, the anteversion angle $\theta$ is obtained by an assumed derotation of the proximal end of the femur to zero degree of anteversion in the AP and Lat projections. This derotation takes place along the femoral shaft axis 14 and with the lateral radiograph plate positioned along the femoral shaft. However, an assumed derotation of the proximal end of the femur to zero degree of anteversion in the AP and Lat projections can also take place along the femoral neck axis 16. This angle of derotation around the femoral neck axis 16 is defined as $\Omega$. The relation between the rotation angle of the femoral neck $\Omega$, the projected cerovicofemoral angles $\alpha$ and $\beta$, the inclination angle $\epsilon$, the deviation angle $\kappa$ and the true femoral neck-shaft angle $\delta$ can be expressed as follows:

$$\sin \Omega = CD/AC = HI/AC$$
$$= \tan \beta o * (AB + AI)/\tan \delta * AB$$

$$\tan \kappa = AI/AD \text{ and } \tan \alpha = AD/AB,$$

therefore $$\sin \Omega = \tan \beta o * (AB + \tan \alpha * \tan \kappa * AB)/\tan \delta * AB$$

$$\sin \Omega = \tan \beta o * (1 + \tan \alpha * \tan \kappa)/\tan \delta$$

$$\tan \delta = AC/AB \text{ and } \cos \Omega = AD/AC,$$

therefore $$\tan \Omega = \tan \beta o * \tan \kappa + \tan \beta o/\tan \alpha$$

where $\kappa$ is the angle of deviation of a central X-ray beam from a direction perpendicular to the femoral neck axis in the lateral projection, and where $\epsilon = \delta \pm \kappa$ If a derotation by $\Omega$ degrees of the femoral neck 10 is assumed to occur, a pin placed along the femoral neck axis will also rotate Ω degrees. If the co-ordinates for the pin position in the digitized radiographs are to be X and Y, a matrix for transformation of co-ordinates in a right-angled co-ordinate system, $$X'=Y^*\sin\Omega+X^*\cos\Omega;$$

$$Y'=Y^*\cos\Omega$$

will give the corrected co-ordinates X' and Y' for a pin/screw position in the straight AP and Lat projections.

FIG. 1 further illustrates distances and angles OADG: Parallel to the film plane 11 in the AP projection 15; OAEF: Parallel to the film plane 13 in the lateral projection 17; OB: Central axis of the femoral neck 10; BC: Central axis of the femoral shaft 18; α: Cervicofemoral angel in the AP projection 15; β: Cervicofemoral angle in the lateral projection 17 when the central X-ray beams are perpendicular to the femoral neck axis 16; βo: Cervicofemoral angle in the lateral projection 17 when the central X-ray beams are not perpendicular to the femoral neck axis 10; ε: The angle of inclination of the central X-ray beams in the lateral projection 17; κ: The angle of deviation of the central X-ray beams in the lateral projection 17 from a direction perpendicular to the femoral neck axis 10; δ: True femoral neck-shaft angles and Ω: Femoral neck rotation angle.

Figure 2:
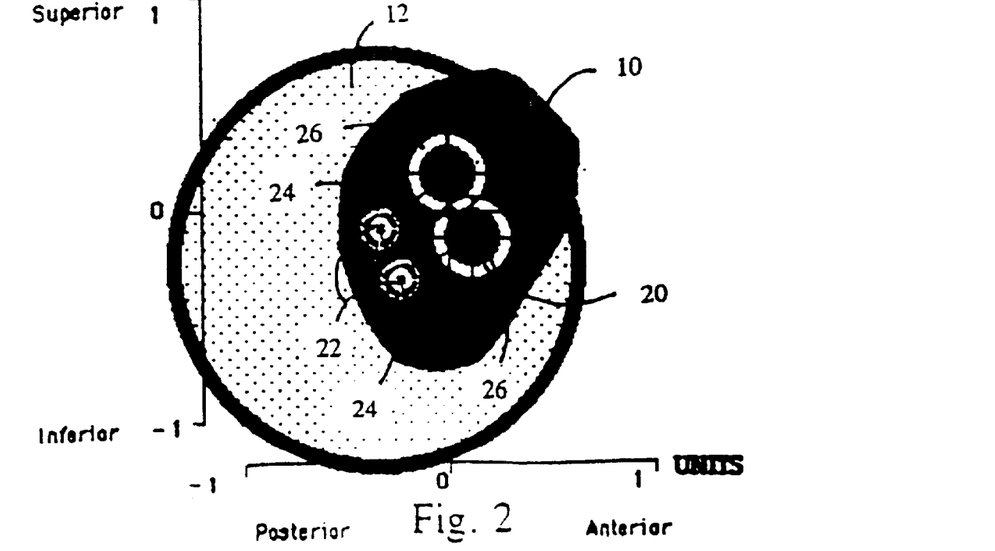
FIG. 2 illustrates a cross-section of a dislocated hip fracture showing symbols for fixating means according to the present invention.
Figure 3:
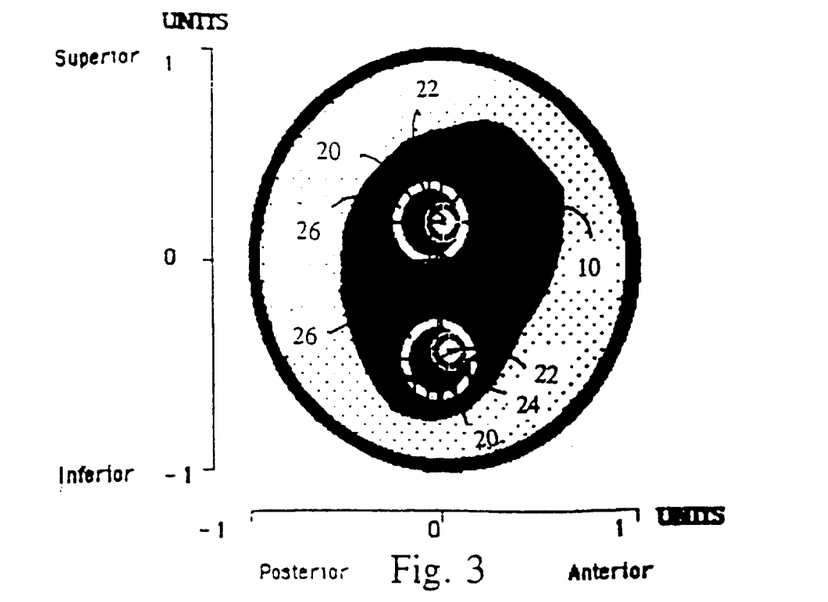
FIG. 3 illustrates a cross-section of a non-dislocated hip fracture displaying symbols for fixating means according to the present invention.

The transformed co-ordinates X' and Y' in the femoral head 12 are plotted in a Cartesian co-ordinate system and circumscribed by a circle with the center placed at the origin of the co-ordinate system, and with the radius equal to that of the femoral head 12 at the measuring point. The obtained graph represents a cross-section of the femoral head at the level of the measuring point, as illustrated in FIG. 2 and FIG. 3 described below.

For the femoral neck 10, the transformed co-ordinates X' and Y' are plotted in a co-ordinate system and circumscribed by cross-section graphs of the femoral neck 10.

If series of radiographs are to be compared to each other, all measured distances are converted from mm to units of measurement by dividing the distance by the diameter of the femoral head 12 on the film in question. The values for pin co-ordinates are expressed as fractions of the femoral head diameter.

In accordance with the present invention hereinafter, a known method named PINTRACE™ has been adapted and developed, to suggest screw positions, in said femoral neck axis 10 and said femoral shaft axis 14 in the AP and Lat radiographs instead of only analyzing already applied screws. The known older method PINTRACE™ was developed by the same inventor as for the present invention and referred to in his thesis "Internal Fixation of Femoral Neck Fractures", Stockholm 1993. ISBN 91-628-0804-4.

In the original older method PINTRACE™, the positions of inserted fixating pins/screws are calculated and presented in constructed cross-sections of the femoral neck 10 and head 12. According to the present invention an entirely new PINTRACE™ method was developed. In fact, the common part between the old known PINTRACE™ and the new PINTRACE™ method is that the configuration according to FIG. 1 is provided in order to make necessary calculations possible. The new PINTRACE™ method is a sub-method to the method of the present invention where the shape of the femoral neck 10 and head 12 are determined, constructed and displayed on, for example, a computer screen as empty cross-section graphs. This allows a surgeon to place symbols for fixating pins/screws, or use displayed predefined positions for such symbols. It should be appreciated that placing symbols is a dynamic task, which varies among patients considering the importance of placing pins/screws as adjacent to the cortex as possible. Positions of provided symbols are transferred to the digitized AP and Lat radiographs and overlaid on these in form of colored lines of varying thickness.

To assist a user in detecting incorrect measurements of the femoral neck radii, (PINTRACE™), according to the present invention, uses a standard neck/head ratio (AP view=0.70, lateral view =0.57: "The proximal end of the femur" thesis by Backman, Karolinska Institutet, Stockholm 1957, and "Anatomy of the Femoral Neck and Head with comparative data from Caucasians and Hong Kong Chinese, Hoaglund and Low, Clin.Orthop 152: 10–16, 1980) for a preview calculation of the femoral neck AP and lateral radii. The user can change the calculated standard radii if they differ from the measured radii on the film in question.

FIG. 2 illustrates a cross-section of a dislocated hip fracture displaying symbols for fixating means, here screws indicated by broken lines and filled circles, according to the present invention.

The cross-section view in FIG. 2 of caput 12 (femoral head) and collum femoris 10 (femoral neck) shows a dislocated hip fracture with two screws attached. Filled black circles 20 represent the position of said screws in collum femoris 10, and filled white circles represent the position of screws in caput 12. Adjacent circles 24, 26 indicate a specific degree of uncertainty for marked up screw positions.

Further, FIG. 3 illustrates a cross section of a non-dislocated hip fracture displaying symbols for fixating means, here screws indicated by broken lines and filled circles, according to the present invention.

The cross-section view in FIG. 3 of caput 12 and collum femoris 10 shows a non-dislocated hip fracture with two screws attached. Filled black circles 20 represent the position of said screws in collum femoris 10, and filled white circles represent the position of screws in caput 12. Adjacent circles 24, 26 indicate a specific degree of uncertainty for marked up screw positions.

Figure 4:
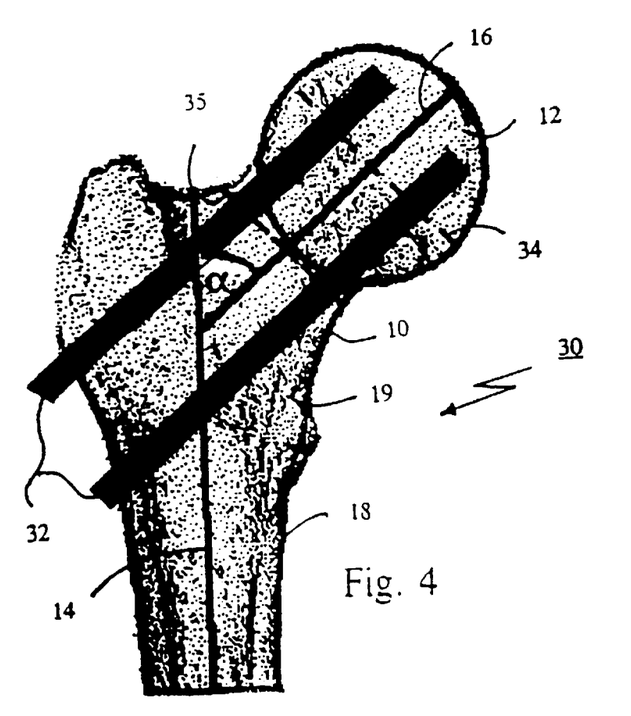
FIG. 4 illustrates a femoral bone structure from its anteroposterior projection with marked screw positions according to the present invention.
Figure 5:
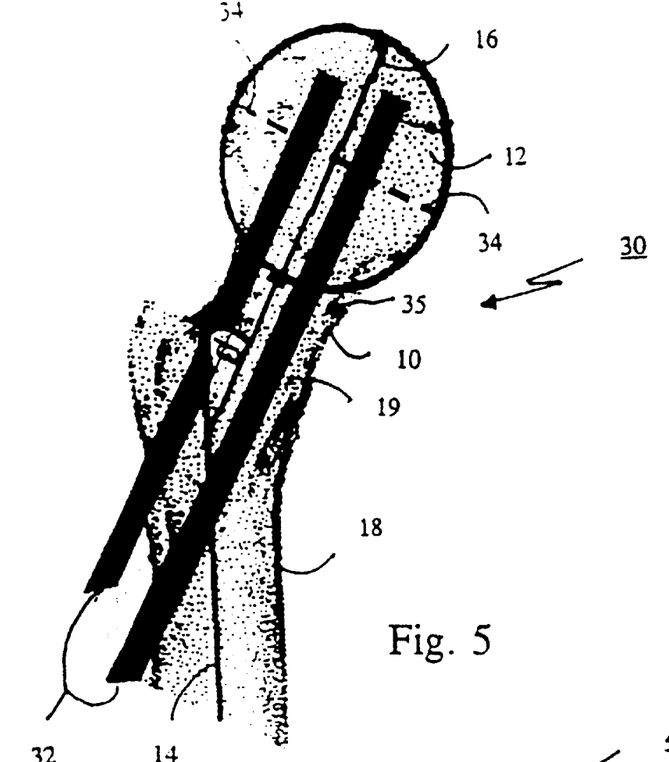
FIG. 5 illustrates a femoral bone structure from its lateral projection with marked screw positions according to the present invention.

Now referring to FIG. 4 and FIG. 5.

FIG. 4 illustrates a femoral bone structure 30 from its anteroposterior projection 15 with two marked screws 32 according to the present invention.

FIG. 5 illustrates a femoral bone structure 30 from its lateral projection 17 with two marked screws 32 according to the present invention.

In the AP and Lat radiograph projections 15, 17 the central axes 14, 16 of the femoral neck 10 and shaft 18 are marked and the femoral neck-angles α and β are measured. The distance from the femoral neck axis 16 to a marker which indicates where to position a screw 32, when surgery is performed, at one measuring points in the Lat view 17 is taken to represent the X co-ordinate and the distance in the AP view 15 the Y co-ordinate for the pin. Angles as shown in FIG. 1, FIG. 4 and FIG. 5 are used to place the femoral bone structure 30 in space, thus finally indicating the direction for insertion of screws 32.

Co-ordinates in the inferior or posterior halves of the femoral bead 12 and neck 10 are assigned negative values, see FIG. 2 and FIG. 3.

For the femoral neck 10, the point of intersection of the femoral head sphere and the femoral neck axis 16 is used as measuring point. The diameters 34, 35, indicated by broken lines in FIGS. 4 and 5, of the femoral head 12 and neck 10 are determined at the measuring points in both the AP and Lat projections 15, 17.

Since magnification factors in the AP and Lat projections often differ, all measured distances are adjusted by calculating the ratio of the greatest and the smallest femoral head diameter and then multiplying the distances in the projection with the smallest diameter by the ratio.

Accordingly, the present invention provides a method for determining, in three dimensions, where to position fixating means in a hip fracture by pre-surgery analysis of at least one anteroposterior and one lateral digitized radiograph of said fracture. It comprises the following steps:

determining a construed femoral shaft axis 14 out off said graphs from at least two midpoints on said shaft axis and drawing a line through said midpoints;

determining a construed femoral neck axis 16 from at least two midpoints on said neck axis and drawing a line through said midpoints;

determining femoral neck angles $\alpha$, $\beta$ determining a femoral head diameter 34 out off said graphs by placing a circle over the perimeter of the femoral head 12;

scaling and rotating said radiographs to a predefined size and position, using an angle between the femoral shaft and an Y-axis in said digitized radiographs, and said diameter 34 of the femoral head 12;

determining the distance from said neck axis 16 and the center of said femoral head, representing a remaining displacement of the hip fracture which is implicitly known from said diameter 34;

measuring the height of the medial cortex 19 out off the anteroposterior graph;

displaying said femoral neck angles $\alpha$, $\beta$;

displaying cross-sections (FIG. 2 and FIG. 3) of the femoral head 12 and neck 10 with a predetermined degree of accuracy;

rotating said cross-sections of the femoral head 12 and neck 10 in order to determine a degree of derotation of the hip, imposed by the fracture, displaying the degree $\Omega$ of hip rotation in said anteroposterior and lateral radiographs; and in one embodiment using said steps in an arrangement in order to determine a position, in three dimensions for attachment of said fixating means 32 and to pre-adjust a tool to work in said position.

Femoral neck-/shaft-angels $\alpha$, $\beta$ are preferably displayed both as lines and as numerical values in said digitized graphs, said lines are automatically re-drawn if the value is changed.

Lines in the present invention are possible to determine with two midpoints, but it should be understood that a more exact line is obtained by drawing a regression line from at least three midpoints on said axes.

Symbols 20, 22 for said fixating means are placed within the cross-section of the femoral neck 10 and a warning function is activated if said fixating means are placed outside of the femoral head 12 or neck 10 in said digitized radiographs.

Fixating means 32 for attachment are automatically displayed in said graphs, through graphical means known per se, with relation to made measurements. Also, it is possible to put down symbols 20, 22 for fixating means 32 in the digitized radiographs.

In accordance with the present invention radiographs are analyzed before any surgical treatment, and measured and computed values can be applied as control input to an arrangement 40 which accomplishes insertion guides, holes for example, for bone fracture fixating means 32, said arrangement 40 being described below.

Figure 6:
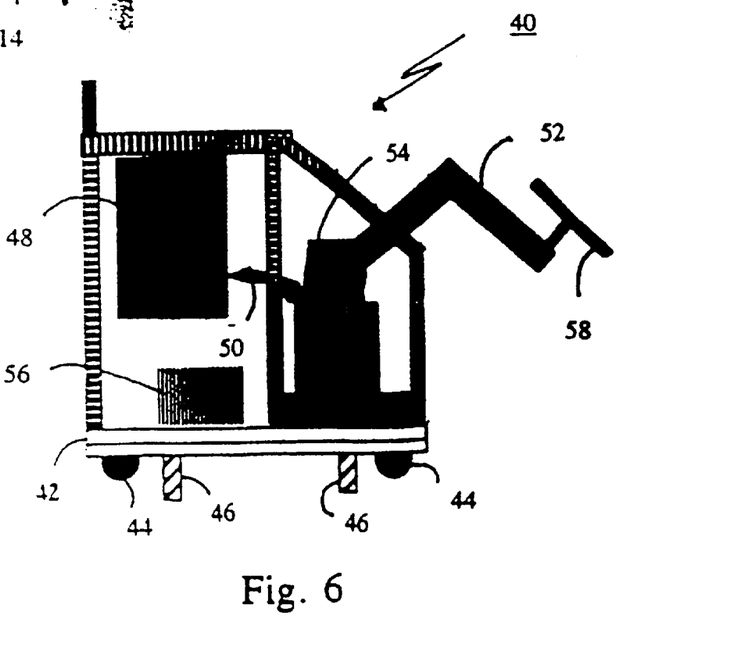
FIG. 6 illustrates a side view elevation of an arrangement according to the present invention.
Figure 7:
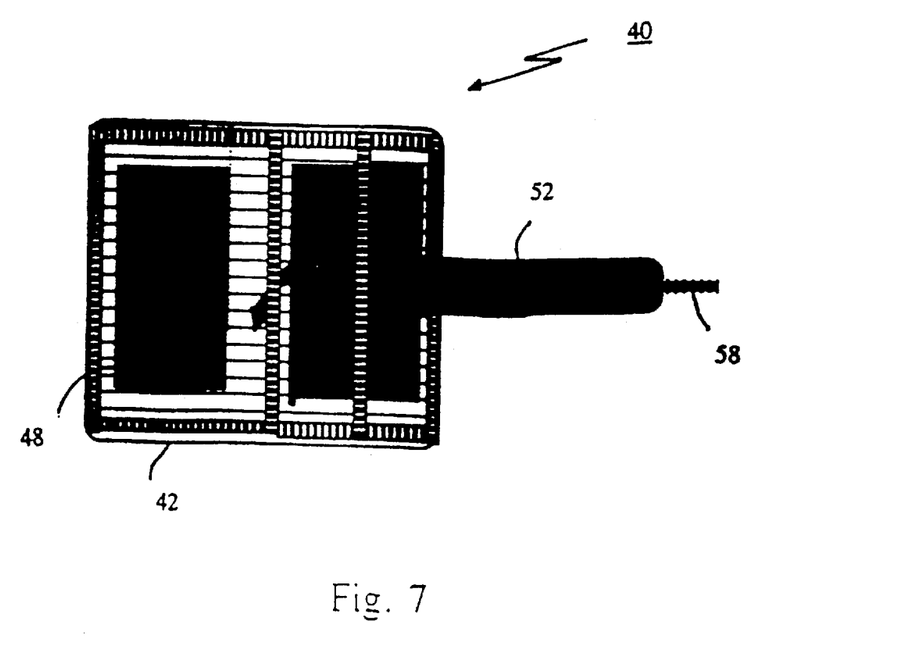
FIG. 7 illustrates a top plan view of an arrangement according to the present invention.
Figure 8:
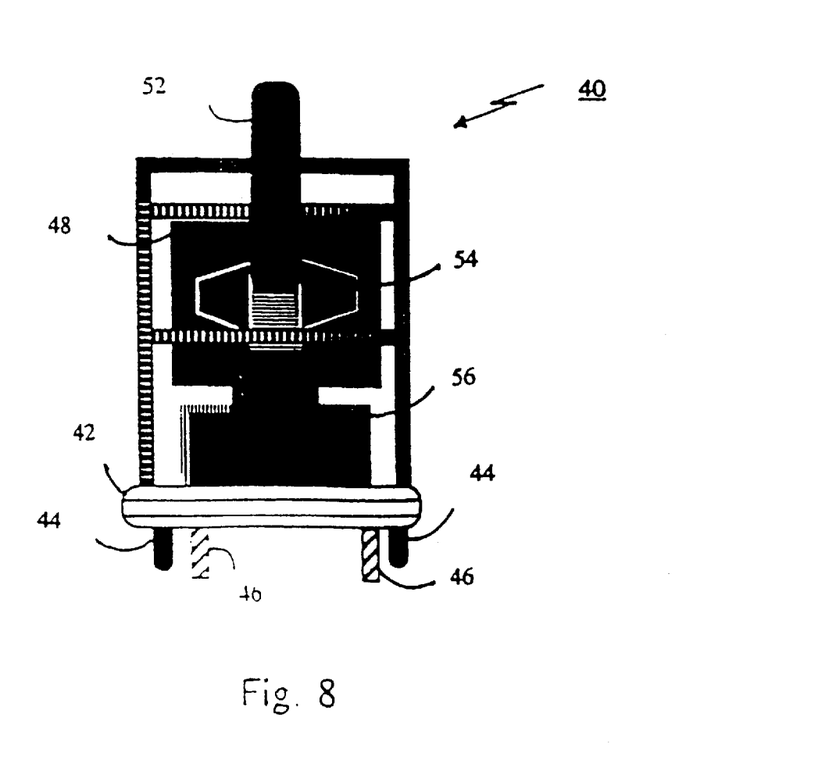
FIG. 8 illustrates a front view elevation of an arrangement according to the present invention.

FIG. 6 illustrates a side view elevation of an arrangement 40 according to the present invention;

FIG. 7 illustrates a top plan view of an arrangement 40 according to the present invention; and FIG. 8 illustrates a front view elevation of an arrangement 40 according to the present invention.

The arrangement 40 according to the embodiment schematically shown in FIGS. 6–8 is a robot on a mobile stand 42 attached with wheels 44 and adjustable feet such as bars, poles 46 or the like for stabilization when ever needed. Further equipment attached, is a control box 48 with a cable link 50 connected to an articulated robot arm 52 with servo or stepper motors 54. A transformer 56 distributes power. The control box 48 is adapted to be connected to peripheral equipment such as a computer with I/O ports for control and communication, a display device, a printer, scanner, frame grabber, and other known computer equipment.

Also, attached on the robot arm 52 is a tool holder 58, for example, used to hold a drilling-machine.

It is comprised in the present invention that said control box 48 for controlling the robot contains hardware devices, firmware devices and software controlled by a processor, each device known per se, but forming an unique entity for applications according to the present invention. Although, in this preferred embodiment of the invention, only one measurement means is described for performing measurements, it is appreciated that measurement means/function can be composed of multiple means, or integrated into one or more means/function as described below according to the present invention.

Thus, in one preferred embodiment comprising means and/or functions, such as: measurement means or function accomplishing measurement of the femoral shaft axis 14 out off said graphs from at least two midpoints on said shaft axis, calculating and drawing a line through said midpoints. Further, the device or function measures a construed femoral neck axis 16 from at least two midpoints on said neck axis, 16, calculating and drawing a line through said midpoints. The femoral neck angles $\alpha$, $\beta$ are determined. Still further, it measures the height of the cortex 19 out off said anteroposterior graph. Also, the means measures, calculates and determines the femoral head diameter 34 out off said graphs by placing a circle over the perimeter of the femoral head 12, and measures, computes or determines the distance from the femoral neck axis 16 to the center of said femoral head 12, representing a remaining displacement of the fracture, which is implicitly known from said femoral head diameter 34, whereby the means measures, calculates and determines the femoral neck diameter 35 out off said graphs by drawing a line, perpendicular to the femoral neck axis, at the intersection of the femoral head sphere and the central femoral neck axis 16;

a scaling function scaling and rotating said radiographs to a predefined size and position, using an angle between the femoral shaft and an Y-axis in a display, displaying co-ordinate axes together with said digitized radiographs, and said femoral head diameter 34;

a display device for displaying data of interest to hip fracture surgery e.g. digitized radiographs, neck angles $\alpha$, hip rotation $\Omega$, cross-sections (FIGS. 2 and 3), computed figures, lines 16, 14, etc.

a function providing displays of said cross-sections of said femoral head 12 and femoral neck 10;

a driver for rotating said cross-sections of the femoral head 12 and neck 10 in order to determine a degree of hip derotation between said head and neck, imposed by the fracture; said means providing control input to a robot with stand means 46 for said robot, tool means on said robot for working in a direction given by said control input, and distortion correcting means (not shown) compensating for x-ray distortion. The distortion compensating means are preferably designed specifically for the present invention or provided through prior art.

X-ray distortion is compensated for with a new inventive method and device for that purpose according to the present invention. The device comprises a plexiglass plate with four lead balls attached and placed in a square pattern. While trans-illuminating in the AP and Lat projections in parallel with the ball pattern, two balls are adjusted to be placed in the center of the radiation field so that they cover each other entirely. Thus, through measuring the distance between the two balls left, an absolute measure of the distortion is determined (the magnification ratio) provided that a predetermined distance between the radiation tube and the plexiglass plate is upheld. This distance corresponds to the working distance when distance determinations are made. A calculation in percentage to adjust the robot arm is finally applied.

Femoral neck angels $\alpha, \beta$ are displayed by said display as lines and numerical values in said digitized graphs. The lines are automatically re-drawn, preferably controlled through software and/or graphic means, if the value is changed.

Symbols 20, 24 for said fixating means are placed within the cross-section of the femoral neck and displayed by said display.

It is included a device or function that activates a warning function if fixating means 32 are placed outside the femoral head or neck in said digitized radiographs.

Further, it is included that fixating means for attachment are automatically displayed in said digitized radiographs with relation to made measurements, by software.

Means, such as graphic drivers, can be provided for putting down symbols for fixating means 20, 24, 32 in the digitized radiographs of the present invention.

The method as herein described is preferably applied to control the robot in using its tool to work in the right direction, and prepare for insertion of fixating means such as screws, pins, nails, etc.

Figure 9:
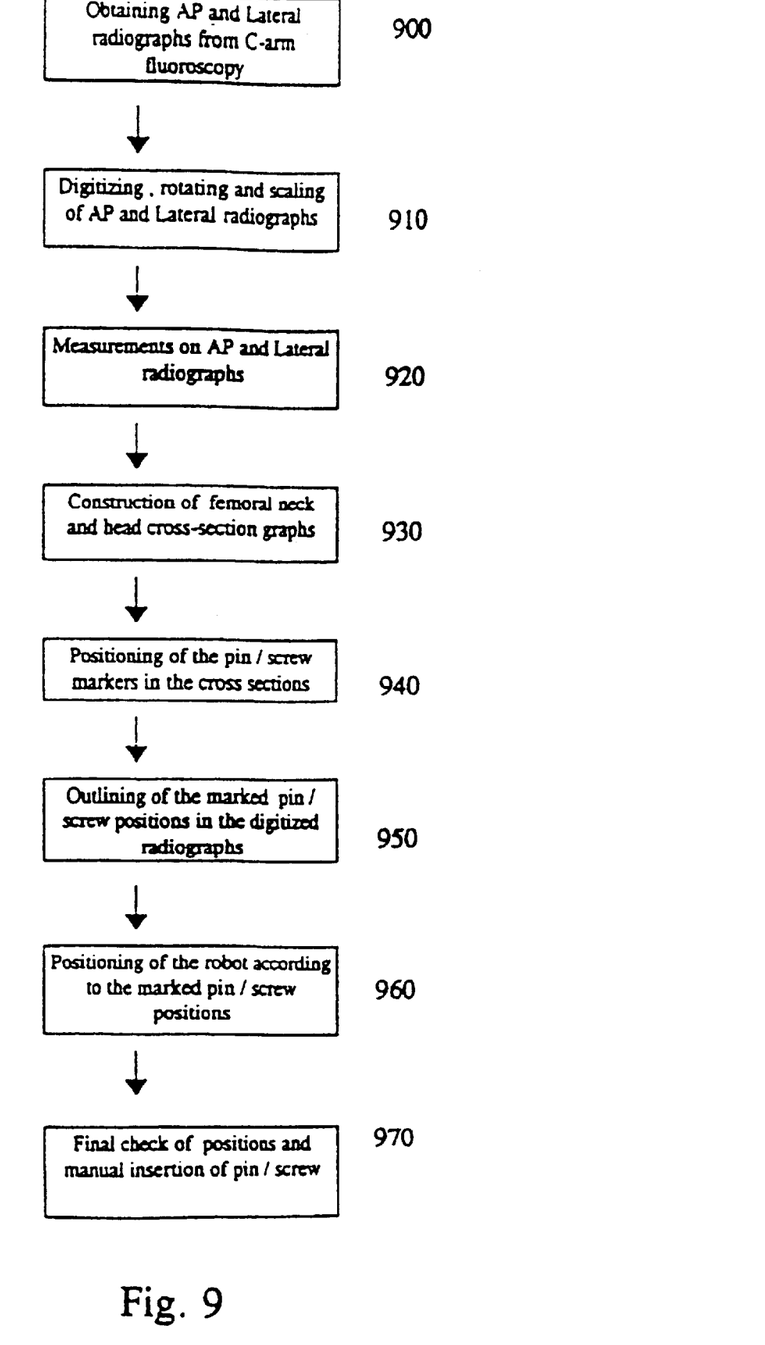
FIG. 9 illustrates a flow chart depicting steps taken in the method of the present invention.

Now referring to FIG. 9, which illustrates a flow chart depicting steps 900 to 980, taken in the method of the present invention, which is applied as control information to an arrangement.

At step 900 AP and Lat radiographs from C-arm fluoroscopy are obtained. The radiographs are digitized, rotated and scaled 910, by drivers for that purpose, followed by performing 920 necessary measurement operations, with means or functions described above, on the radiographs of a hip fracture.

Made measurements are resulting in construction 930, through a software, of femoral neck and head cross-section graphs, which are displayed on a screen. Displayed cross-sections are marked 940 with pin/screw markers, which are changeable through software. An outlining 950 of the marked pin/screw positions in the digitized radiographs is thus performed.

The steps 900–950 are applied to position 960 a robot to drill in said positions. This is followed up by a final check of determined positions. Eventually, during surgery, a surgeon manually inserts 980 pins/screws.

Accordingly it should be understood that the PIN-TRACE™ method or like methods are adapted to the method described in accordance with the flow chart.

It is thus believed that the operation and construction of the present invention will be apparent from the foregoing description. While the method and arrangement shown or described has been characterized as being preferred it will be obvious that various changes and modifications may be made therein without departing from the spirit and scope of the invention as defined in the following claims.

What is claimed is:

1. A method for determining, in three dimensions, where to position a fixating device in a hip fracture structure by pre-surgery analysis of at least one anteroposterior and one lateral digitized radiograph of said fracture, said method comprising:

determining a construed femoral shaft axis out of said graphs from at least two midpoints on said shaft axis and drawing a line through said midpoints;

determining a construed femoral neck axis from at least two midpoints on said neck axis and drawing a line through said midpoints;

determining femoral neck angles ($\alpha, \beta$);

determining a femoral head diameter out of said graphs by placing a circle over the perimeter of the femoral head;

scaling and rotating said radiographs to a predefined size and position, using an angle between the femoral shaft and a Y-axis in said digitized radiographs, and said diameter of the femoral head;

determining a femoral neck diameter out of said radiographs by drawing a line, perpendicular to the femoral neck axis, at the intersection of the femoral head sphere and the central femoral neck axis;

determining the distance from said neck axis and the center of said femoral head perpendicular to the femoral neck axis, representing a remaining displacement of the hip fracture which is implicitly known from said head diameter;

measuring the height of the medial cortex out of the anteroposterior graph;

displaying said femoral neck angles ($\alpha, \beta$);

displaying cross-sections of the femoral head and femoral neck with a predetermined degree of accuracy;

rotating said cross-sections of the femoral head and femoral neck in order to determine a degree of derotation of the hip, imposed by the fracture;

displaying the degree of hip rotation in said anteroposterior and lateral radiographs; and using said steps in order to determine a position, in three dimensions, for attachment of said fixating device.

2. A method according to claim 1, wherein the femoral neck angles ($\alpha, \beta$) are displayed as lines and numerical values in said digitized graphs, said lines are automatically re-drawn if a value is changed.

3. A method according to claim 1, wherein symbols for said fixating device are placed within the cross-section of the femoral neck.

4. A method according to claim 3, wherein a warning function is activated if said fixating device is placed outside the femoral head or femoral neck in said digitized radiographs.

5. A method according to claim 3, wherein the fixating device for attachment is automatically displayed in said graphs with relation to previously made measurements.

6. A method according to claim 1, wherein a device is provided for putting down symbols for fixating means in said digitized radio graphs.

7. A method, according to claim 2, wherein said lines are regression lines drawn from at least three midpoints.

8. An arrangement providing for attachment of a fixating means in a hip fracture structure, through analyzing at least one anteroposterior and one lateral digitized radiograph of said fracture, comprising:

measurement means for determining a femoral shaft axis out of said graphs from at least two midpoints on said shaft axis, and drawing a line through said midpoints;

measurement means for determining a femoral neck axis from at least two midpoints on said neck axis and drawing a line through said midpoints;

measurement means for determining femoral neck angles ($\alpha$, $\beta$);

measurement means for determining a femoral head diameter out of said graphs by placing a circle over the perimeter of said femoral head;

measurement means determining a femoral neck diameter out of said radiographs by drawing a line, perpendicular to the femoral-neck axis, at the intersection of the femoral head sphere and the central femoral neck axis;

driver means for scaling and rotating said radiographs to a predefined size and position, using an angle between the femoral shaft and a Y-axis in said digitized radiographs, and said femoral head diameter;

measurement means for determining the distance from the femoral-neck axis to the center of said femoral head perpendicular to the femoral neck axis, representing a remaining displacement of the fracture, which is implicitly known from said femoral head diameter;

measurement means for determining the height of the medial cortex out of said anteroposterior graph;

display means for displaying said neck angles ($\alpha$, $\beta$);

display means for providing displays of cross-sections of said femoral head and femoral neck with a predetermined degree of accuracy, driver means for rotating said cross-sections of the femoral head and femoral neck in order to determine a degree of hip derotation ($\Omega$) between said femoral head and femoral neck, imposed by the fracture, and display means for displaying said hip rotation in said anteroposterior and lateral radiographs, said display means providing control input to a robot with tool means on said robot for working in a direction given by said control input, and distortion correcting means compensating for x-ray distortion.

9. An arrangement according to claim 8, wherein the femoral neck angles ($\alpha$, $\beta$) are displayed, by said display means for displaying said neck angles, as lines and numerical values in said digitized graphs, said lines are automatically re-drawn if a value is changed.

10. An arrangement according to claim 8, wherein symbols for said fixating means are placed within the cross-section of the femoral neck and displayed by said means for displaying.

11. An arrangement according to claim 10, wherein a warning function is activated if said fixating means is placed outside said femoral head or femoral neck in the digitized radiographs.

12. An arrangement according to claim 10, wherein said fixating means for attachment is automatically displayed in said graphs with relation to previously made measurements.

13. An arrangement according to claim 8, wherein means are provided for putting down symbols for fixating means in said digitized radiographs.

14. An arrangement according to claim 9, wherein said lines are regression lines drawn from at least three midpoints.

15. An arrangement providing for attachment of a fixation device in a hip fracture structure, through analyzing at least one anteroposterior and one lateral digitized radiograph of said fracture, comprising:

a measurement device to determine a femoral shaft axis out of said graphs from at least two midpoints on said shaft axis, and drawing a line through said midpoints;

a measurement device to determine a femoral neck axis from at least two midpoints on said neck axis and drawing a line through said midpoints;

a measurement device to determine femoral neck angles ($\alpha$, $\beta$);

a measurement device to determine a femoral head diameter out of said graphs by placing a circle over the perimeter of said femoral head;

a measurement device to determine a femoral neck diameter out of said radiographs by drawing a line, perpendicular to the femoral-neck axis, at the intersection of the femoral head sphere and the central femoral neck axis;

a driver device to scale and rotate said radiographs to a predefined size and position, using an angle between the femoral shaft and a Y-axis in said digitized radiographs, and said femoral head diameter;

a measurement device to determine the distance from the femoral neck axis to the center of said femoral head perpendicular to the femoral neck axis, representing a remaining displacement of the fracture, which is implicitly known from said femoral head diameter;

a measurement device to determine the height of the medial cortex out of said anteroposterior graph;

a display to display said neck angles ($\alpha$, $\beta$);

a display to provide displays of cross-sections of said femoral head and femoral neck with a predetermined degree of accuracy, a driver device to rotate said cross-sections of the femoral head and femoral neck in order to determine a degree of hip derotation ($\Omega$) between said femoral head and femoral neck, imposed by the fracture, a display to display said hip rotation in said anteroposterior and lateral radiographs, said display provides control input to a robot with a tool on said robot for working in a direction given by said control input, and a distortion correcting device for compensating for x-ray distortion.

16. An arrangement according to claim 15, wherein femoral neck angles ($\alpha$, $\beta$) are displayed as lines and numerical values in said digitized graphs, said lines are automatically re-drawn if a value is changed.

17. An arrangement according to claim 15, wherein symbols for said fixation device are placed within the cross-section of the femoral neck and displayed by said display.

18. An arrangement according to claim 17, wherein a warning function is activated if said fixation device is placed outside said femoral head or femoral neck in the digitized radiographs.

19. An arrangement according to claim 17, wherein said fixation device is automatically displayed in said graphs with relation to previously made measurements.

20. An arrangement according to claim 15, wherein a device is provided for putting down symbols for said fixation device in said digitized radiographs.

21. An arrangement according to claim 16, wherein said lines are regression lines drawn from at least three midpoints.

* * * * *